United States Patent [19]

Eliachar

[11] Patent Number: 5,350,396
[45] Date of Patent: Sep. 27, 1994

[54] NASAL SPLINT

[75] Inventor: Isaac Eliachar, Pepper Pike, Ohio

[73] Assignee: Hood Laboratories, Pembroke, Mass.

[21] Appl. No.: 48,842

[22] Filed: Apr. 15, 1993

[51] Int. Cl.$^5$ .............................................. A61F 5/04
[52] U.S. Cl. ...................................... 606/199; 602/5; 602/17; 606/196
[58] Field of Search ............... 606/196, 199, 204.45, 606/232, 201, 204; 128/858, 201.18; 602/5, 6, 17

[56] References Cited

U.S. PATENT DOCUMENTS

| | | | |
|---|---|---|---|
| 3,935,859 | 2/1976 | Doyle | 606/196 |
| 4,201,217 | 5/1980 | Slater | 606/199 |
| 4,592,357 | 6/1986 | Ersek | 606/199 |
| 5,094,233 | 3/1992 | Brennan | 606/199 X |

Primary Examiner—Richard J. Apley
Assistant Examiner—Beverly A. Meindl
Attorney, Agent, or Firm—Kane, Dalsimer, Sullivan, Kurucz, Levy, Eisele and Richard

[57] ABSTRACT

A nasal splint is described to separate the mucoperiosteum within a nasal cavity. The splint includes an elongate base sized and shaped to separate the inferior conchae. A flexible wing extends away from the base to separate the walls of the middle conchae when the splint is in place within the nasal cavity. A hollow tube is also provided on the base for defining an air passage.

6 Claims, 2 Drawing Sheets

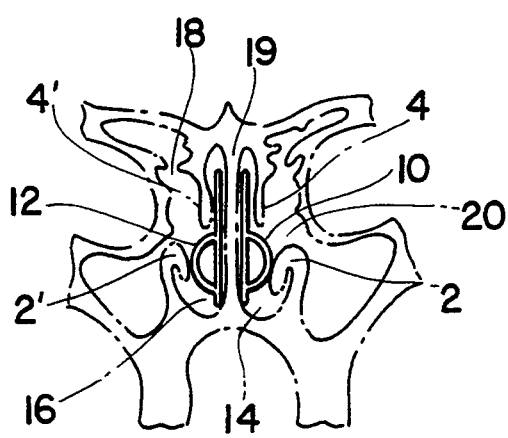
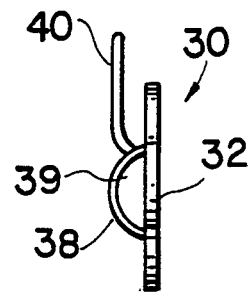
FIG. 1
PRIOR ART
FIG. 2
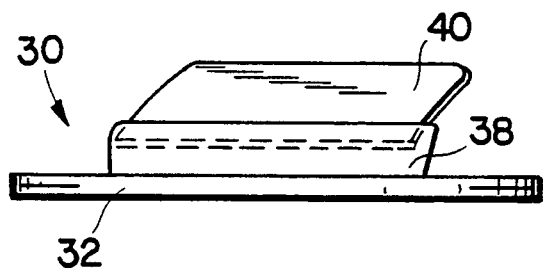
FIG. 3
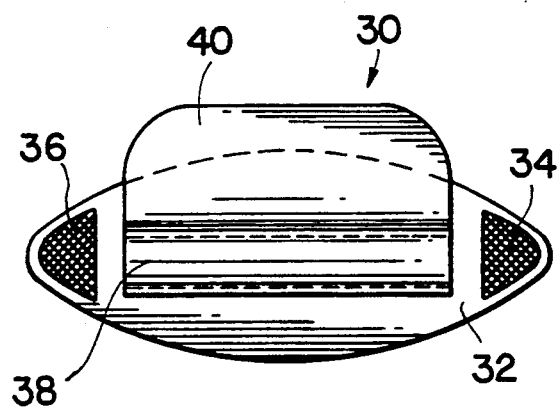
FIG. 4
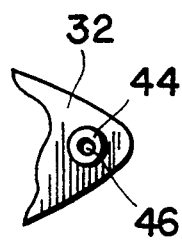
FIG. 6

NASAL SPLINT

BACKGROUND OF THE INVENTION

1. Field of the Invention

This invention pertains to a splint used in a nasal cavity after surgery or injury to prevent mucosal membranes lining the nasal septum and conchae from scarring and adhering to each other.

2. Description of the Related Art

Frequently after surgery or certain injuries, various mucosal membranes of the nasal cavity scar and/or adhere to each other thereby impeding the nasal passages and normal breathing of the patient. This occurrence may be prevented, at least partially, by the use of commercially available nasal splints. One such splint consists of a trapezoidal, planar device made of polyethylene or Teflon ® and which is inserted into the nasal cavity beneath the lateral turbinate. The splint is sutured in place. After several weeks the splint is removed. Another type of splint consists of an oval, planar member sutured in place with a semicircular lumen attached thereto to form an airway path. This splint, shown in the FIG. 1 of the accompanying drawings, is made of a medical grade silicon rubber. The problem with these splints is that they only serve to protect the mucosal membranes covering the concha nasalis inferior ossea (referred to hereinafter as the inferior turbinate). The membranes covering the other concha nasalis ossea (turbinates) remain unprotected.

SUMMARY OF THE INVENTION

In view of the above-mentioned disadvantages of prior art devices, it is an objective of the present invention to provide a nasal splint which insures a more complete separation of the nasal mucosal membranes after surgery or injury.

A further objective is to provide a splint which may be easily tailored to the needs and anatomical characteristics of each patient.

Another objective is to provide an inexpensive but effective nasal splint.

Other objectives and advantages of the invention shall become apparent from the following description. Briefly, a nasal splint constructed in accordance with the present invention comprises of a base having a generally oval shape with means for affixing the splint inside a normal nasal cavity. Secured to the base is a hollow tube oriented to form a breathing passage for a patient while the splint is in the nasal cavity. A wing-shaped member extends outwardly from the base or tube, parallel with their longitudinal axis, at an angle transverse to the aforesaid longitudinal axis. When inserted into a nasal passage with the base disposed below the lateral turbinate, the wing extends into the nasal middle meatus to separate the interior mucosal membrane walls.

More particularly, the invention comprises a nasal splint for protecting the mucoperiosteum covering nasal conchae in a human nasal cavity, which comprises;

(a) a base portion, which comprises a planar sheet with a first outer surface, an opposite, second outer surface, a first end, an opposite, second end and a longitudinal axis extending on a straight line from the first to the second end; said sheet surfaces being oval shaped with the length being co-extensive with the longitudinal axis; said base portion being of a size adapted to be received in a human nasal cavity with the first surface oriented towards the perpendicular plate of ethmoid bone;

(b) a hollow tube portion connected to the second surface of the base portion on a line parallel to said straight line, said hollow tube having a first open end, a second open end and a tubular body extending between the open ends, said tubular body being of a size to bridge the space between said base portion and the inferior turbinate when said splint is received in said nasal cavity; and (c) a wing portion connected to the base portion and extending outwardly to a wing edge, from said base portion on an angle transverse to said straight line a pre-determined distance, said wing being of a size and said angle being such as to position said wing edge in the space between the middle turbinate and the middle meatus when said splint is received in said nasal cavity.

BRIEF DESCRIPTION OF THE DRAWINGS

FIG. 1 shows a coronal view through a typical human nasal cavity with prior art nasal splints installed in place in left and right nasal passages.

FIG. 2 shows an end view of a nasal splint constructed in accordance with this invention;

FIG. 3 shows a side view of the nasal splint of FIG. 2;

FIG. 4 shows a plan view of the nasal splint of FIG. 2;

FIG. 6 shows an alternate embodiment of the invention.

DETAILED DESCRIPTION OF THE INVENTION

Figure 5:
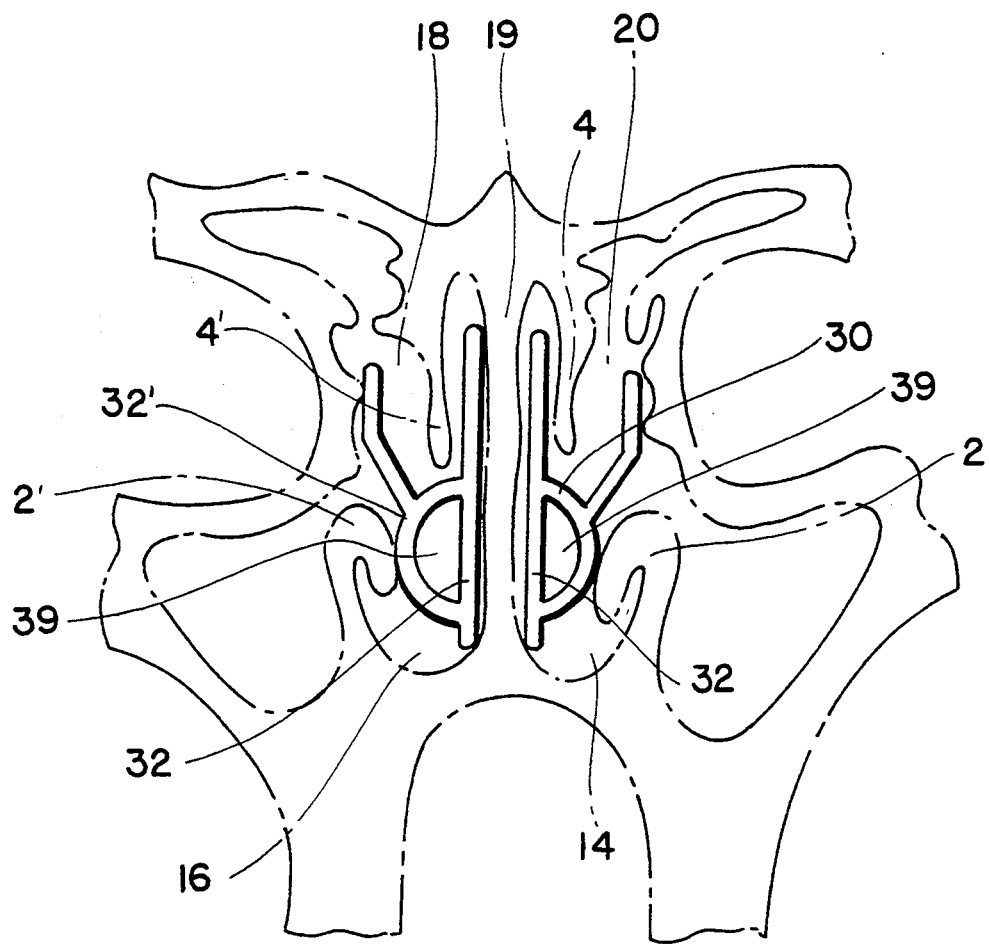
FIG. 5 shows a coronal view similar to FIG. 1 but enlarged with the nasal splint of FIGS. 2-4 installed in place.

As shown in FIG. 1, prior art splints 10, 12 have been inserted into left and right nasal cavities 14, 16 respectively. Each of the splints 10, 12 is disposed in the space between the inferior 2, 2' and middle 4, 4' turbinates (lateral turbinates) and the perpendicular plate 19 of the ethmoid bone. As can be clearly seen in the FIG. 1, the walls of the left and right nasal middle meatus 18, 20 are unsupported and each therefore the mucosal membrane covering these walls is free to adhere together and scar.

Referring now to FIG. 4, the nasal splint 30 constructed in accordance with this invention includes a base portion 32 which is a flat sheet and has a generally oval shape, somewhat like a flattened football. At the narrow ends, base portion 32 is provided with meshed areas 34, 36, used as a means of securing the splint 30 to the nasal septum. Between these meshed areas 34, 36 the splint 30 is formed with a longitudinal semi-circular tube 38; see FIG. 2, a side elevation. Tube 38 defines an air passage or lumen 39 which functions as an airway by-pass through the nasal cavity 14 or 16 when the splint 30 is positioned in the nasal cavity.

The splint 30 also includes a wing 40. Wing 40 may be attached to the base 32, or to the tube 38 as shown best in FIG. 3, a side view. The wing 40 extends angularly away from tube 38, parallel to the longitudinal axis of tube 38. The angle is transverse to the longitudinal axis of the tube 38.

Instead of meshed areas 34, 36 base 32 may be provided with a rubber grommet 44 having an aperture 46 therein. The grommet 44 provides extra support and strength to base portion 32 as shown in FIG. 6, a partial view of an alternate embodiment splint 30 of the invention. The alternate embodiment splint may be secured in the nasal cavity by suturing (passing the suture through aperture 46).

FIG. 5, a coronal view of a human nasal cavity, shows two splints 30, 30' of the invention, each inserted into the left and right nasal cavities, respectively. While base portion 32 and lumen 39 are in substantially the same position as the prior art splints 10, 12 shown in FIG. 1, wings 40, 40' each extend into the left or right nasal middle meatus 18, 20 to insure that their walls are separated and the covering mucosal membrane does not scar or adhere together.

Preferably the splints 30, 30' are each made of medical grade silicon rubber so that they are soft, pliable and safe to use as part of a post-operative procedure. The splints 30, 30' are shaped to fit into the normal human nasal cavity and if necessary are easy to cut to size and shape.

Generally, base 32 will have a length of about 3-9/16 inches, a width of about 1-3/8 inches and a thickness of about 0.4 to 0.45 inches. The tube 38 advantageously has a length of about 2-3/16 inches and lumen 39 an inner diameter of about 8 mm.

Obviously numerous other modifications may be made to the invention without departing from its scope as defined in the appended claims.

I claim:

1. A nasal splint for protecting the mucoperiosteum covering the middle turbinates and the inferior turbinates in a human nasal cavity, which comprises;
   (a) a base portion, which comprises a planar sheet with a first outer surface, an opposite, second outer surface, a first end, an opposite, second end and a longitudinal axis extending on a straight line from the first to the second end; said sheet surfaces being oval shaped with the length being co-extensive with the longitudinal axis; said base portion being of a size adapted to be received in a human nasal cavity with the first surface oriented towards the perpendicular plate of ethmoid bone;
   (b) a hollow tube portion connected to the second surface of the base portion on a line parallel to said straight line, said hollow tube having a first open end, a second open end and a tubular body joined to the second surface of the base portion so as to form a closed portion with respect to said second surface extending between the open ends, said tubular body being of a size to bridge the space between said base portion and the inferior turbinate when said splint is received in said nasal cavity;
   said tubular body defining an open lumen within the tube which lumen has a longitudinal axis on a line between the first and second open ends, said longitudinal axis being parallel to the longitudinal axis of the base portion described above; and
   (c) a wing portion connected to the base portion and extending outwardly to a wing edge, from said base portion on an angle transverse to said straight line a predetermined distance, said wing being of a size and said angle being such as to position said wing edge in the space between the middle turbinate and the middle meatus when said splint is received in said nasal cavity.

2. The splint of claim 1 further comprising means on the base portion for securing said base within said nasal cavity.

3. The splint of claim 2 wherein said means includes a meshed area on said base.

4. The splint of claim 2 wherein said means includes a hole in said base portion and a grommet reinforcing said hole in the base portion, inserted into said hole.

5. The splint of claim 1 wherein said angle is acute and the wing edge is distal to the base portion first end and proximal to the base portion second end.

6. The splint of claim 1 wherein the wing portion connection is through the hollow tube body.

* * * * *